United States Patent [19]

Love et al.

[11] 4,172,079

[45] Oct. 23, 1979

[54] PREPARATION OF 4-NITROISOXAZOLES

[75] Inventors: Richard F. Love, Fishkill, N.Y.;
Roger G. Duranleau, Georgetown, Tex.

[73] Assignee: Texaco Inc., White Plains, N.Y.

[21] Appl. No.: 865,105

[22] Filed: Dec. 27, 1977

Related U.S. Application Data

[63] Continuation-in-part of Ser. No. 685,250, May 11, 1976, abandoned.

[51] Int. Cl.² .......................................... C07D 261/14
[52] U.S. Cl. .................................................... 548/245
[58] Field of Search .................................. 260/307 H

[56] References Cited

U.S. PATENT DOCUMENTS

| | | | |
|---|---|---|---|
| 2,517,893 | 8/1950 | Larchar et al. | 252/171 |
| 2,564,423 | 8/1951 | Barnum | 106/14 |
| 3,415,856 | 12/1968 | Lachowicz et al. | 260/413 |
| 3,691,189 | 9/1972 | Saucy | 260/307 H |
| 3,818,029 | 6/1974 | Regel et al. | 260/307 H |
| 3,995,048 | 11/1976 | Nadelson | 260/307 H |
| 4,061,651 | 12/1977 | Love et al. | 260/307 H |

OTHER PUBLICATIONS

"Heterocyclic Compounds", (isoxazoles), Interscience, (1962), p. 19.
Morrison et al., "Organic Chemistry", (1966), pp. 854, 870, 1075.

*Primary Examiner*—David Wheeler
*Attorney, Agent, or Firm*—Thomas H. Whaley; Carl G. Ries; George J. Darsa

[57] ABSTRACT

4-nitroisoxazoles are prepared by reacting an alpha-nitroketone with a hydroximyl halide in the presence of a tertiary amine.

18 Claims, No Drawings

PREPARATION OF 4-NITROISOXAZOLES

CROSS REFERENCE TO RELATED APPLICATION

This application is a continuation-in-part of our co-pending application Ser. No. 685,250 filed May 11, 1976 now abandoned.

BACKGROUND OF THE INVENTION

This invention relates to a method of preparing 4-nitroisoxazoles. In particular, this invention relates to a novel method of preparing nitroisoxazoles in a single step by reacting a nitroketone and a hydroximyl halide.

Nitroisoxazoles can be prepared by initially forming a 1,2-oxazole and thereafter nitrating the 4-position. One method for preparing 1,2-oxazoles is by cyclization of monooximes of betadiketones with the simultaneous elimination of water. Nitration of the 4-position involves reaction of the 1,2-oxazoles with nitric acid suitably in the presence of sulfuric acid at elevated temperatures. While such a two-step method provides some yield of the desired 4-nitroisoxazole, the starting materials are usually highly reactive and frequently form a mixture of products that are not readily separated. Further, the nitration step is in many instances nonselective in nitrating the 4-position, as for example when the oxazole contains acyl or phenyl substituents. When nitration of a phenyl isoxazole is conducted, a mixture of aryl and isoxazole nitro-substituted products are formed. Nitration of, for example, 3-acyl-5-alkylisoxazoles oxidizes the acyl group to a carboxylic acid group. It appears, therefore, that such a method is applicable to the preparation of a limited number of nitroisoxazoles. Consequently, the method is not particularly economical or commercially attractive inasmuch as, in general, low yields of desired product are provided.

It is therefore an object of this invention to provide a novel method for preparing 4-nitroisoxazoles.

Another object of this invention is to provide a method for preparing 4-nitroisoxazoles in good yields.

Yet another object of this invention is to provide a method for preparing a wide range of 4-nitroisoxazoles in a single step.

Other objects and advantages will become apparent from the following detailed description and examples.

SUMMARY OF THE INVENTION

Broadly, this invention contemplates a method of preparing 4-nitroisoxazoles which comprises contacting an alpha-nitroketone with a hydroximyl halide in the presence of a tertiary amine.

Pursuant to this invention, the contemplated 4-nitroisoxazoles are prepared from 1-nitro-2-alkanones corresponding to the formula:

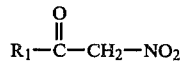

where $R_1$ is an alkyl group having from 1 to 30 carbon atoms, suitably 1 to 20 carbons and preferably 4 to 20 carbons. Illustrative of the starting materials, we mention 1-nitro-2-propanone, 1-nitro-2-butanone, 1-nitro-2-pentanone, 1-nitro-2-hexanone, 1-nitro-2-heptanone, 1-nitro-2-octanone, 1-nitro-2-decanone, 1-nitro-2-dodecanone, 1-nitro-2-pentadecanone, 1-nitro-2-hexadecanone, 1-nitro-2-heptadecanone, 1-nitro-2-eicosanone, and 1-nitro-2-heneicosanone. The alpha-nitroketones contemplated as reactants herein can be prepared by methods known to the art, as for example the procedure described in U.S. Pat. No. 3,415,856. Essentially, the procedure involves a nitrooxidation reaction by contacting a 1-olefin with dinitrogen tetroxide and oxygen to form a peroxy intermediate and thereafter contacting the peroxy compound with a denitrating agent. Internal nitroketones, that is, nitroketones prepared from other than 1-olefins or from cyclic alkenes and where the nitro group is on other than a terminal carbon or where an alpha-nitrocycloalkanone is formed, do not react in the instant method to produce the 4-nitroisoxazoles.

The second component contemplated in the present method is a hydroximyl halide corresponding to the formula:

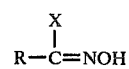

where R may be an aryl, an alkyl, an acyl (alkanoyl) or an aroyl group having from 1 to 20 carbon atoms, suitably from 5 to 20 carbon atoms and where X is chlorine, bromine, iodine or fluorine. It will be understood that when R is aryl the group has 6 to 20 carbons, when alkyl 1 to 20 carbons, when alkanoyl 2 to 20 carbons and when aroyl 7 to 20 carbons. Illustrative of the starting materials, we mention acetylhydroximyl chloride, acetylhydroximyl bromide, acetylhydroximyl iodide, acetylhydroximyl fluoride, butanoylhydroximyl chloride, pentanoylhydroximyl bromide, hexanoylhydroximyl chloride, nonanoylhydroximyl chloride, undecanoylhydroximyl chloride, undecanoylhydroximyl bromide, undecanoylhydroximyl iodide, undecanoylhydroximyl fluoride, tridecanoylhydroximyl chloride, benzoylhydroximyl chloride, 2-methylbenzoylhydroximyl chloride, phenylhydroximyl chloride, (benzhydroximic acid chloride) tolylhydroximyl chloride, tertiary butylphenylhydroximyl chloride, butylhydroximyl chloride, ethylhydroximyl bromide, pentylhydroximyl fluoride, octylhydroximyl iodide, dodecylhydroximyl chloride and hexadecylhydroximyl chloride. Aryl and alkyl hydroximyl halides can be prepared by reacting the corresponding oxime with a halogen in a corresponding halogen acid. Acyl (alkanoyl) and aroyl hydroximyl halides can be prepared by reacting the corresponding nitroketone with a halogen acid in an organic acid.

More specifically, the process of this invention comprises reacting an alpha-nitroketone with a hydroximyl halide as hereinabove described in the presence of a tertiary amine. The contemplated amines include aliphatic or aromatic or heterocyclic amines corresponding to the formula:

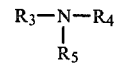

where $R_3$, $R_4$, and $R_5$ are alkyl, cycloalkyl or aryl groups or where $R_3$, $R_4$, and/or $R_5$ together with the nitrogen (N) are heterocyclic and where $R_3$, $R_4$, and $R_5$ are from 1 to 12 carbons, preferably from 1 to 6 carbons, and where the sum of $R_3$, $R_4$, and $R_5$ is from 3 to 36 carbons. Also contemplated as tertiary amines and employed in the method are tetraalkyl substituted $C_2$ and C5 alkylene diamines and tetraalkyl substituted guanidines, where the tetraalkyl groups are from 1 to 6 carbons. Illustrative of the tertiary amines contemplated in the instant method, we mention tertiary aliphatic, alicyclic and aromatic amines including N-butyldidodecylamine, N,N-diethylcyclohexylamine, N,N-diethyldodecylamine, N,N-dimethylaniline, N,N-dimethylbenzylamine, N,N-dimethyloctylamine, N,N-diisopropylethylamine, N,N-dimethylethylamine, N,N-diethylmethylamine, N,N-dimethylpropylamine, N,N-diethylpropylamine, N,N-ethylmethylpropylamine, N-ethyldibenzylamine, tributylamine, tridodecylamine, triethylamine, trihexylamine, trimethylamine, tricyclohexylamine, tetramethylethylenediamine, tetramethylpropylenediamine, tetramethylguanidine and tetraethylguanidine. Heterocyclic compounds contemplated include pyridine, methylpiperidine, 2-ethylpyridine, 1,4-dimethylpiperazine, 4-ethylpyridine, 2,4-ludidine, 3-picoline, 2,4,6-trimethylpyridine and quinoline. The preferred tertiary compounds are trimethylamine, triethylamine, pyridine, methylpiperidine, N,N-dimethylethylamine, N,N-diethylmethylamine, N,N-dimethylpropylamine, N,N-diethylpropylamine, N,N-ethylmethylpropylamine and tetramethylguanidine. Highly preferred compounds are the trialkylamines, triethylamine and diethylmethylamine and also tetramethylguanidine and pyridine.

In the practice of the instant invention, the alpha-nitroketone, hydroximyl halide and tertiary amine are admixed. To promote the contact of the reactants, the reaction is desirably carried out under conditions of agitation in the presence of a non-reactive organic solvent. Solvents for the reactions include any in which the reactants are soluble and in which preferably amine hydrohalides, such as triethylamine hydrochloride, are insoluble. In general, the solvents possess a boiling point between about 30 and 100° C. or higher and we prefer to use such materials as n-hexane, n-heptane, diethylether, benzene, dioxane and tetrahydrofuran. Excessive amounts of tertiary amines having a boiling point between about 30° and 100° C. can also be employed as the solvent.

Pursuant to our method, the nitroketone, hydroximyl halide and tertiary amine are contacted, preferably in the presence of a solvent, in a mole ratio of hydroximyl halide to nitroketone of between about 1:1 and 1:5, preferably between about 1:1 and 1:1.1. The amount of tertiary amine employed can vary over a wide range since it may be present as an initial reaction component and additionally as a solvent. In general, mole ratios of nitroketone to tertiary amine of about 1:1 and 1:50 and higher, preferably between about 1:1 and 1:5, are utilized. The use of a solvent enables the reactants to be solubilized thereby shortening the reaction time and improving yields of the 4-nitroisoxazole. When a solvent is employed, the formation of an insoluble amine hydrohalide by-product permits high conversion to the desired product and the products are easily recovered from the reaction mixture. In general, reaction times are from one quarter to twenty-four hours; employing reaction temperatures of from −10° to 50° C. lead to the high production of desired product. At the completion of the reaction, the tertiary amine can be separated as the hydrohalide suitably by filtration or evaporation at reduced pressures. The solvent can be removed by, for example, low pressure distillation. The 4-nitroisoxazole can be recovered from any unreacted components by crystallization.

The 4-nitroisoxazoles prepared according to this invention correspond to the formula:

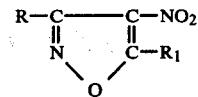

where R and $R_1$ are as defined above. Illustrative of the 4-nitroisoxazoles provided by the method include 3-acetyl-4-nitro-5-methylisoxazole, 3-propyl-4-nitro-5-methylisoxazole, 3-hexyl-4-nitro-5-decylisoxazole, 3-octanoyl-4-nitro-5-hexylisoxazole, 3-undecyl-4-nitro-5-octadecylisoxazole, 3-tridecanoyl-4-nitro-5-octylisoxazole, 3-pentadecanoyl-4-nitro-5-tetradecylisoxazole, 3-phenyl-4-nitro-5-octylisoxazole, 3-phenyl-4-nitro-5-dodecylisoxazole, 3-benzoyl-4-nitro-5-tetradecylisoxazole, 3-benzoyl-4-nitro-5-octylisoxazole, 3-tolyl-4-nitro-5-butylisoxazole, 3-[tertiary butylphenyl]-4-nitrodecylisoxazole and 3-[2-methylbenzoyl]-4-nitro-5-heptylisoxazole.

The 4-nitroisoxazoles prepared by the method of this invention are useful as corrosion inhibitors, such as those described in U.S. Pat. No. 2,564,423, and as additives to fuels and lubricants. The compounds can also be used as additives in cleaning and degreasing compositions as in U.S. Pat. No. 2,517,893. The compounds are also useful as intermediates in the preparation of isoxazolyl sulphanilamides as in CA 81 120523s (1974) and described as bacteriostats and fungistats. Other derivatives have been converted to sulfur drugs as described in, for example, Musante, Gazz. Chim. Ital. 71 565 (1941). The preparation of other valuable products as amine derivatives are reported to have biological and physiological activity and other derivatives are useful as photograhic sensitizers and dyes for color photography. The isoxazoles can also be converted to pyrazoles, Ber., 45 3041 (1912) which are useful as metal complexing agents, Chem. Rev. 72 499 (1972).

In order to more fully illustrate the nature of our invention and the manner of practicing the same, the following examples are presented.

EXAMPLE 1

A solution of tridecanoylhydroximyl chloride (1.5 grams, 5.4 mmoles) in 50 milliliters (0.47 mole) of diethylether was added dropwise over a 30 minute period to a stirred blend of 1-nitro-2-decanone (1.0 gram, 5 mmole) and triethylamine (1.2 gram, 12 mmoles) in 50 milliliters of diethylether. After stirring for eighteen hours, the mixture was filtered and a white precipitate of triethylamine hydrochloride was collected (0.65 gram, 94 percent yield). The filtrate was evaporated to dryness under 25 millimeters pressure leaving 2.20 grams (100 percent yield) of a yellow-brown crystalline solid having a melting point of 44°–46° C. Recrystallization from petroleum ether afforded 1.85 grams (84 percent yield) of a material having a melting point of 46.5°–47.5° C. Infrared spectral and nuclear magnetic resonance analyses identified the product as 3-tridecanoyl-4-nitro-5-octylisoxazole.

EXAMPLE 2

Following the procedure described in Example 1, benzhydroximic acid chloride (1.6 grams, 10 mmoles), previously prepared by the chlorination of benzaldehyde oxime in hydrochloric acid, was reacted with 1-nitro-2-decanone (2.0 grams, 10 mmoles) and triethylamine (2.0 grams, 20 mmoles) in 50 milliliters of diethylether. Triethylamine hydrochloride was collected as a precipitate (1.31 grams, 95 percent yield). The crude isoxazole was recrystallized from petroleum ether-diethylether and subsequently methanol to obtain 2.5 grams (83 percent yield) of pale yellow crystals having a melting point of 42°-43° C. The product was identified by infrared and nuclear magnetic resonance as 3-phenyl-4-nitro-5-octylisoxazole.

EXAMPLE 3

Following the procedure described in Example 1, omega-chloroisonitrosoacetophenone (phenacylhydroximyl chloride) (1.83 grams, 10 mmoles), previously prepared from omega-chloroacetophenone by reaction with butylnitrite was reacted with 1-nitro-2-hexadecanone (2.85 grams, 10 mmoles) and triethylamine (2.0 grams, 20 mmoles) in 150 milliliters of diethylether. The triethylamine hydrochloride precipitate was collected (1.4 grams, 100 percent yield). After stripping the ether from the filtrate, the residue (4.1 gram) was recrystallized from methanol to afford 3.35 grams (81 percent yield) of product. Infrared spectral analysis identified the product as 3-benzoyl-4-nitro-5-tetradecylisoxazole, m.p. 36°-37° C.

EXAMPLE 4

Employing the procedure used in Example 3, omega-chloroisonitrosoacetophenone (phenacylhydroximyl chloride) (1.83 grams, 10 mmoles) was reacted with 1-nitro-2-decanone (2.0 grams, 10 mmoles) and triethylamine (2.0 grams, 20 mmoles) in diethylether. Triethylamine hydrochloride (1.35 grams, 98 percent) was recovered along with 2.46 grams (77 percent yield) of an uncrystallizable red oil. Infrared and nuclear magnetic resonance analyses indicated the product to be 3-benzoyl-4-nitro-5-octylisoxazole.

EXAMPLE 5

Phenylhydroximyl chloride (1.55 grams, 10 mmoles) was reacted with 1-nitro-2-tetradecanone (2.61 grams, 10 mmoles) and triethylamine (2.0 grams, 20 mmoles) in 100 milliliters of diethylether. The triethylamine hydrochloride formed was collected (1.32 grams, 96 percent yield). The crude nitroisoxazole obtained (4.0 grams, net) was recrystallized from methanol to afford 2.71 grams (76 percent yield) of material having a melting point of 53°-54° C. and identified by infrared to be 3-phenyl-4-nitro-5-dodecylisoxazole.

EXAMPLE 6

Pentadecanoylhydroximyl chloride (2.93 grams, 10 mmoles) and 1-nitro-2-hexadecanone (2.85 grams, 10 mmoles) and triethylamine (2.0 grams, 20 mmoles) in 200 milliliters of diethylether were stirred for 7 hours. Triethylamine hydrochloride (1.36 grams, 98 percent) was recovered and the product after recrystallization from methanol afforded 3.1 grams (59 percent) of a material having a melting point of 67°-68° C. and identified as 3-pentadecanoyl-4-nitro-5-tetradecylisoxazole.

We claim:

1. A method of preparing 4-nitroisoxazoles which comprises the step of contacting an alpha-nitroketone corresponding to the formula:

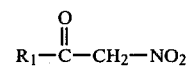

where $R_1$ is an alkyl group having from 1 to 30 carbon atoms with a hydroximyl halide corresponding to the formula:

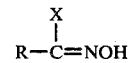

where R is an aryl group having 6 to 20 carbon atoms, an alkyl group having 1 to 20 carbon atoms, an alkanoyl group having 2 to 20 carbon atoms or an aroyl group having 7 to 20 carbon atoms and where X is chlorine, bromine, iodine or fluorine in the presence of a tertiary amine corresponding to the formula:

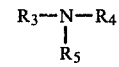

where $R_3$, $R_4$ and $R_5$ are alkyl, cycloalkyl or aryl groups or where $R_3$, $R_4$ and or $R_5$ together with N are heterocyclic, where $R_3$, $R_4$ and $R_5$ groups have 1 to 12 carbon atoms and where the sum of $R_3$, $R_4$ and $R_5$ is 3 to 36 carbon atoms or tetraalkyl substituted $C_2$ and $C_5$ alkylene diamines and tetraalkyl substituted guanidines, where the tetraalkyl groups have 1 to 6 carbon atoms at a temperature of from about $-10°$ to $50°$ C., wherein the mole ratio of said hydroximyl halide to said nitroketone is between about 1:1 and 1:5.

2. A method according to claim 1 wherein said nitroketone is 1-nitro-2-hexanone.

3. A method according to claim 1 wherein said nitroketone is 1-nitro-2-decanone.

4. A method according to claim 1 wherein said nitroketone is 1-nitro-2-dodecanone.

5. A method according to claim 1 wherein said nitroketone is 1-nitro-2-tetradecanone.

6. A method according to claim 1 wherein said nitroketone is 1-nitro-2-hexadecanone.

7. A method according to claim 1 wherein said hydroximyl halide is tridecanoylhydroximyl chloride.

8. A method according to claim 1 wherein said hydroximyl halide is phenylhydroximyl chloride.

9. A method according to claim 1 wherein said hydroximyl halide is phenacylhydroximyl chloride.

10. A method according to claim 1 wherein said hydroximyl halide is pentadecanoylhydroximyl chloride.

11. A method according to claim 1 wherein said hydroximyl halide is acetylhydroximyl chloride.

12. A method according to claim 1 wherein said tertiary amine is a trialkylamine, wherein said alkyl groups have from 1 to 12 carbon atoms.

13. A method according to claim 1 wherein said tertiary amine is triethylamine.

14. A method according to claim 1 wherein said tertiary amine is diethylmethylamine.

15. A method of preparing 4-nitroisoxazoles which comprises the step of contacting an alpha-nitroketone corresponding to the formula:

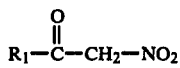

where $R_1$ is an alkyl group having from 1 to 30 carbon atoms with a hydroximyl halide corresponding to the formula:

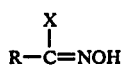

where R is an aryl group having 6 to 20 carbon atoms, an alkyl group having 1 to 20 carbon atoms, an alkanoyl group having 2 to 20 carbon atoms or an aroyl group having 7 to 20 carbon atoms and where X is chlorine, bromine, iodine or fluorine in the presence of tetramethyl guanidine at a temperature of from about $-10°$ to $50°$ C. wherein the mole ratio of said hydroximyl halide to said nitroketone is between about 1:1 and 1:5.

16. A method of preparing 4-nitroisoxazoles which comprises the step of contacting an alpha-nitroketone corresponding to the formula:

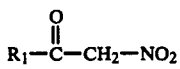

where $R_1$ is an alkyl group having from 1 to 30 carbon atoms with a hydroximyl halide corresponding to the formula:

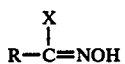

where R is an aryl group having 6 to 20 carbon atoms, an alkyl group having 1 to 20 carbon atoms, an alkanoyl group having 2 to 20 carbon atoms or an aroyl group having 7 to 20 carbon atoms and where X is chlorine, bromine, iodine or fluorine in the presence of pyridine at a temperature of from about $-10°$ to $50°$ C. wherein the mole ratio of said hydroximyl halide to said nitroketone is between about 1:1 and 1:5.

17. A method according to claim 1 wherein said contacting is conducted in the presence of a reaction inert organic solvent having a boiling point between about $30°$ and $100°$ C.

18. A method of preparing 4-nitroisoxazoles which comprises the step of contacting an alpha-nitroketone corresponding to the formula:

where $R_1$ is an alkyl group having from 1 to 30 carbon atoms with a hydroximyl halide corresponding to the formula:

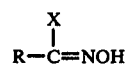

where R is an alkanoyl group having 2 to 20 carbon atoms or an aroyl group having 7 to 20 carbon atoms and where X is chlorine, bromine, iodine or fluorine in the presence of a tertiary amine having 3 to 36 carbon atoms, wherein said amine is a tetraalkyl substituted $C_2$ to $C_5$ alkylene diamine, a $C_1$ to $C_6$ tetraalkyl substituted guanidine, N,N-dimethylaniline, N,N-dimethylbenzylamine, N-ethyldibenzylamine, tricyclohexylamine, pyridine, methylpiperidine, 2-ethylpyridine, 1,4-dimethylpiperazine, 4-ethylpyridine, 2,4-ludidine, 3-picoline, 2,4,6-trimethylpyridine or quinoline at a temperature of from about $-10°$ to $50°$ C. wherein the mole ratio of said hydroximyl halide to said nitroketone is between about 1:1 and 1:5.

* * * * *